United States Patent
Itoh et al.

(10) Patent No.: US 10,849,595 B2
(45) Date of Patent: Dec. 1, 2020

(54) IMAGING APPARATUS FOR DIAGNOSIS AND PROGRAM

(71) Applicant: TERUMO KABUSHIKI KAISHA, Tokyo (JP)

(72) Inventors: Ema Itoh, Hadano (JP); Isao Mori, Chofu (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 1391 days.

(21) Appl. No.: 14/872,187

(22) Filed: Oct. 1, 2015

(65) Prior Publication Data

US 2016/0095577 A1    Apr. 7, 2016

Related U.S. Application Data

(63) Continuation of application No. PCT/JP2013/002384, filed on Apr. 5, 2013.

(51) Int. Cl.
  *A61B 8/00* (2006.01)
  *A61B 8/12* (2006.01)
  (Continued)

(52) U.S. Cl.
  CPC ........ *A61B 8/4416* (2013.01); *A61B 5/02007* (2013.01); *A61B 8/12* (2013.01);
  (Continued)

(58) Field of Classification Search
  None
  See application file for complete search history.

(56) References Cited

U.S. PATENT DOCUMENTS

| | | | |
|---|---|---|---|
| 9,770,172 B2 * | 9/2017 | Sturm | A61B 5/0037 |
| 2003/0103212 A1 * | 6/2003 | Westphal | A61B 3/102 |
| | | | 356/479 |

(Continued)

FOREIGN PATENT DOCUMENTS

| | | |
|---|---|---|
| JP | 11-56752 A | 3/1999 |
| JP | 2010-508973 A | 3/2010 |
| JP | 2010-516304 A | 5/2010 |
| WO | WO 2008/086613 A1 | 7/2008 |
| WO | WO 2010/103718 A1 | 9/2010 |

OTHER PUBLICATIONS

International Search Report (PCT/ISA/210) dated May 7, 2013, by the Japanese Patent Office as the International Searching Authority for International Application No. PCT/JP2013/002384.

*Primary Examiner* — Angela M Hoffa
*Assistant Examiner* — Helene Bor
(74) *Attorney, Agent, or Firm* — Buchanan Ingersoll & Rooney PC

(57) ABSTRACT

An imaging apparatus is disclosed for diagnosis including a plurality of transmitting and receiving units, an error of a scale of a tomographic image to be generated is reduced. The imaging apparatus can include including acquisition means for acquiring a propagation velocity of an ultrasound signal of a flushing liquid, generation means for generating ultrasound line data based on the propagation velocity of the ultrasound signal in a blood vessel tissue, and conversion means for converting positional information of each position within a range in which the flushing liquid flows regarding the ultrasound line data generated by the generation means based on a ratio between the propagation velocity in the blood vessel tissue and the propagation velocity in the flushing liquid. A tomographic image of a blood vessel is constructed by using the ultrasound line data converted by the conversion means.

10 Claims, 11 Drawing Sheets

(51) Int. Cl.
*A61B 8/08* (2006.01)
*A61B 5/02* (2006.01)
*A61B 8/14* (2006.01)
*A61B 5/00* (2006.01)

(52) U.S. Cl.
CPC ............... *A61B 8/14* (2013.01); *A61B 8/445* (2013.01); *A61B 8/4427* (2013.01); *A61B 8/4444* (2013.01); *A61B 8/4461* (2013.01); *A61B 8/4483* (2013.01); *A61B 8/4488* (2013.01); *A61B 8/4494* (2013.01); *A61B 8/462* (2013.01); *A61B 8/5223* (2013.01); *A61B 8/5261* (2013.01); *A61B 8/56* (2013.01); *A61B 5/0035* (2013.01); *A61B 8/5207* (2013.01); *A61B 8/54* (2013.01)

(56) References Cited

U.S. PATENT DOCUMENTS

| | | | |
|---|---|---|---|
| 2007/0078343 A1* | 4/2007 | Kawashima | A61B 8/5238 600/443 |
| 2008/0161696 A1* | 7/2008 | Schmitt | A61B 5/0066 600/467 |
| 2008/0177138 A1 | 7/2008 | Courtney et al. | |
| 2011/0245683 A1* | 10/2011 | Onimura | A61B 5/0066 600/476 |
| 2012/0063570 A1 | 3/2012 | Furuichi et al. | |
| 2012/0253184 A1* | 10/2012 | Furuichi | A61B 5/7425 600/425 |
| 2017/0086793 A1* | 3/2017 | Sato | A61B 8/488 |

* cited by examiner

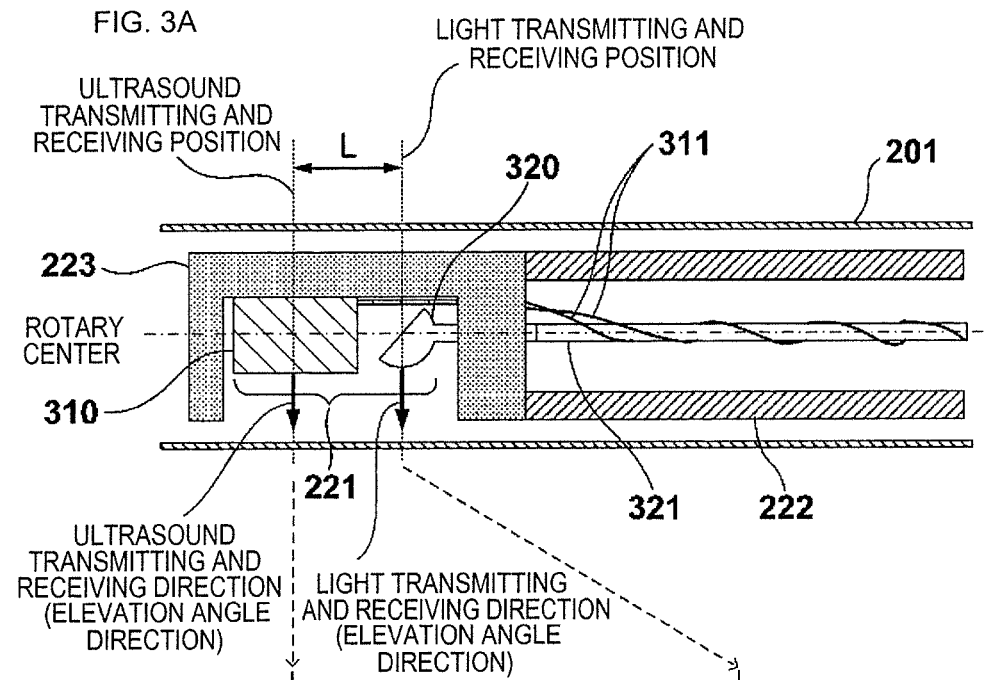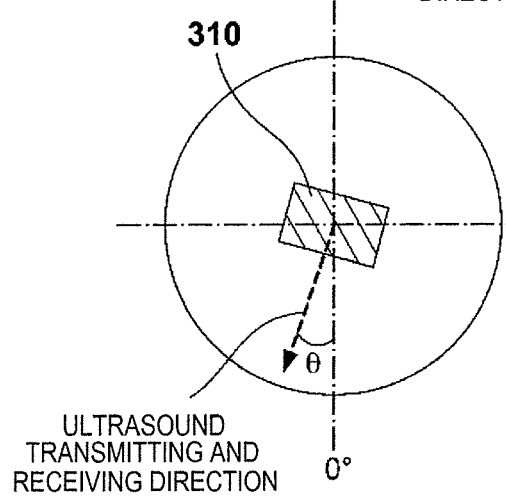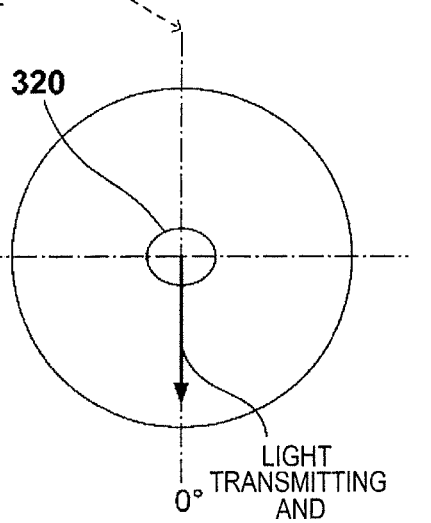

IMAGING APPARATUS FOR DIAGNOSIS AND PROGRAM

CROSS-REFERENCES TO RELATED APPLICATIONS

This application is a continuation of International Application No. PCT/JP2013/002384 filed on Apr. 5, 2013, the entire content of which is incorporated herein by reference.

TECHNICAL FIELD

The present disclosure relates to an imaging apparatus for diagnosis, and a program.

BACKGROUND DISCUSSION

Imaging apparatuses for diagnosis have been widely used to perform diagnoses of arteriosclerosis, and to perform preoperative diagnoses or to check postoperative results when intra-vascular treatment is performed using a high-performance catheter such as a balloon catheter and a stent.

The imaging apparatus for diagnosis can include an ultrasound tomography apparatus for diagnosis (IVUS: intra-vascular ultrasound), and an optical coherent tomography apparatus for diagnosis (OCT: optical coherence tomography), which are different from one another in characteristics.

In addition, recently, an imaging apparatus for diagnosis (an imaging apparatus for diagnosis including an ultrasound transmitting and receiving unit which can transmit and receive ultrasounds, and a light transmitting and receiving unit which can transmit and receive light) in which a function of the IVUS and a function of the OCT are combined together has been proposed (for example, refer to JP-A-11-56752 and JP-T-2010-508973). According to such an imaging apparatus for diagnosis, both a tomographic image (an ultrasound tomographic image) utilizing the characteristics of the IVUS, which can measure a high depth region, and a tomographic image (an optical coherent tomographic image, hereinafter, referred to as "an optical tomographic image") utilizing the characteristics of the OCT, which can perform measurement at a high resolution, by performing scanning once can be constructed.

SUMMARY

When transmitting and receiving light with the light transmitting and receiving unit, there is a need to perform flushing for replacing blood in a blood vessel by using a flushing liquid. Therefore, in a case of an imaging apparatus for diagnosis in which a function of IVUS and a function of OCT are combined together, ultrasounds output from an ultrasound transmitting and receiving unit are transmitted toward a flushing liquid (not blood).

There are various types of flushing liquids, and each of the flushing liquids has a propagation velocity of ultrasounds, which are different from one another. Therefore, when flushing is performed with the flushing liquids, which are different from one another, there is an occurrence of an error of the scale of a generated ultrasound tomographic image.

For such a reason, in a case of an imaging apparatus for diagnosis in which the function of the IVUS and the function of the OCT are combined together, in order to reduce the error of the scale of an ultrasound tomographic image, it is important to consider the propagation velocity of ultrasounds in each region on the transmitting and receiving path of ultrasounds and to construct the ultrasound tomographic image.

An imaging apparatus is disclosed for diagnosis including a plurality of transmitting and receiving units, in which an error of the scale of the tomographic image to be constructed can be reduced.

An imaging apparatus is disclosed for diagnosis constructing a first tomographic image and a second tomographic image inside a lumen of a measurement subject body by using an ultrasound signal which is transmitted and received by a first transmitting and receiving unit and an optical signal which is transmitted and received by a second transmitting and receiving unit in a case where a transmitting and receiving unit in which the first transmitting and receiving unit performing transmission and reception of the ultrasound signal and the second transmitting and receiving unit performing transmission and reception of the optical signal are disposed moves in an axial direction while rotating in the lumen of the measurement subject body, the apparatus including acquisition means for acquiring a propagation velocity of the ultrasound signal in a medium flowing inside the lumen; generation means for generating ultrasound line data indicating strength of a reflection signal from each position in a transmitting and receiving direction of the ultrasound signal based on a predetermined propagation velocity; and conversion means for converting positional information of each position within a range in which the medium flows regarding the ultrasound line data generated by the generation means based on a ratio between the predetermined propagation velocity and the propagation velocity which is acquired by the acquisition means, in which the first tomographic image is constructed by using the ultrasound line data which is converted by the conversion means.

An imaging apparatus is disclosed for diagnosis constructing a first tomographic image and a second tomographic image inside a lumen of a measurement subject body by using an ultrasound signal which is transmitted and received by a first transmitting and receiving unit and an optical signal which is transmitted and received by a second transmitting and receiving unit in a case where a transmitting and receiving unit in which the first transmitting and receiving unit performing transmission and reception of the ultrasound signal and the second transmitting and receiving unit performing transmission and reception of the optical signal are disposed moves in an axial direction while rotating in the lumen of the measurement subject body, the apparatus comprising: acquisition means for acquiring a propagation velocity of the ultrasound signal in a medium flowing inside the lumen; generation means for generating ultrasound line data indicating strength of a reflection signal from each position in a transmitting and receiving direction of the ultrasound signal, based on the propagation velocity acquired by the acquisition means; and conversion means for converting positional information of each position on an outer side from a range in which the medium flows regarding the ultrasound line data generated by the generation means, based on a ratio between a predetermined propagation velocity and the propagation velocity which is acquired by the acquisition means, wherein the first tomographic image is constructed by using the ultrasound line data which is converted by the conversion means.

A method is disclosed of controlling an image processing apparatus, which processes an image of a target object constructing a first tomographic image and a second tomographic image inside a lumen of a measurement subject body by using an ultrasound signal which is transmitted and received by a first transmitting and receiving unit and an optical signal which is transmitted and received by a second transmitting and receiving unit in a case where a transmitting and receiving unit in which the first transmitting and receiving unit performing transmission and reception of the ultrasound signal and the second transmitting and receiving unit performing transmission and reception of the optical signal are disposed moves in an axial direction while rotating in the lumen of the measurement subject body, the method comprising: acquiring a propagation velocity of the ultrasound signal in a medium flowing inside the lumen; generating ultrasound line data indicating strength of a reflection signal from each position in a transmitting and receiving direction of the ultrasound signal based on a predetermined propagation velocity; converting positional information of each position within a range in which the medium flows regarding the ultrasound line data generated based on a ratio between the predetermined propagation velocity and the propagation velocity; and constructing the first tomographic image by using the ultrasound line data from the converting of the positional information According to the present disclosure, an error of the scale of a tomographic image to be constructed in an imaging apparatus for diagnosis having a plurality of transmitting and receiving units can be reduced.

Other features and advantages of the present disclosure will be clearly described below with reference to the accompanying drawings. In the accompanying drawings, the same reference numerals and signs will be applied to the same or similar constitutions.

BRIEF DESCRIPTION OF THE DRAWINGS

The accompanying drawings are incorporated in this disclosure, take part in the constitution, illustrate embodiments of the present disclosure, and are used to describe the principle of the present disclosure together with the disclosure thereof.

FIG. 3A is a diagram illustrating a cross-sectional constitution of an imaging core, and a disposition of an ultrasound transmitting and receiving unit and a light transmitting and receiving unit.

FIG. 3B is a cross-sectional view when being cut on a plane, which is substantially orthogonal to the rotary center axis at an ultrasound transmitting and receiving position.

FIG. 3C is a cross-sectional view when being cut on a plane, which is substantially orthogonal to the rotary center axis at the light transmitting and receiving position.

DETAILED DESCRIPTION

Hereinafter, each embodiment of the present disclosure will be described in detail with reference to the accompanying drawings as necessary. The embodiments described below are preferable specification examples of the present disclosure and are subjected to various limitations which are technically preferable. However, the scope of the present disclosure is not limited to those aspects unless otherwise specified so as to particularly limit the present disclosure in the following description.

1. Constitution of Appearance of Imaging Apparatus for Diagnosis

Figure 1:
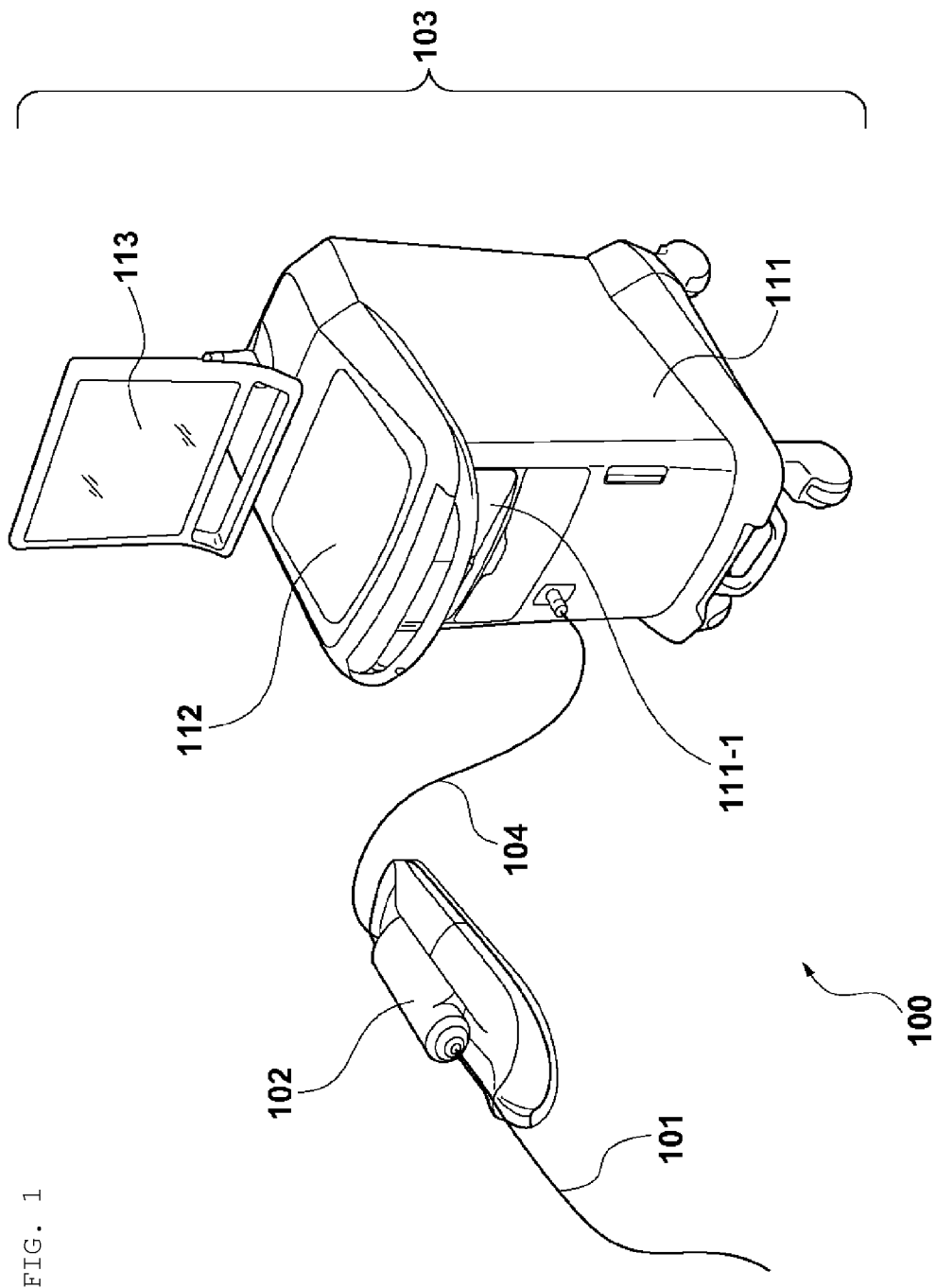
FIG. 1 is a diagram illustrating a constitution of the appearance of an imaging apparatus for diagnosis according to an embodiment of the present disclosure.

FIG. 1 is a diagram illustrating a constitution of the appearance of an imaging apparatus 100 for diagnosis (an imaging apparatus for diagnosis including a function of IVUS and a function of OCT) according to an embodiment of the present disclosure. As illustrated in FIG. 1, the imaging apparatus 100 for diagnosis can include a probe unit 101, a scanner and pull-back unit 102 and an operation control device 103. The scanner and pull-back unit 102 and the operation control device 103 are connected to each other through a signal wire 104 so as to be able to transfer various signals.

An imaging core which is directly inserted into a blood vessel (a lumen of a measurement subject body) is interpolated into the probe unit 101. The imaging core can include an ultrasound transmitting and receiving unit which transmits ultrasounds based on a pulse signal into a blood vessel and receives reflected waves (reflection signals) from the inside of the blood vessel, and a light transmitting and receiving unit which continuously transmits transferred light (measurement light) into a blood vessel and continuously receives reflected light (reflection signals) from the inside of the blood vessel. In the imaging apparatus 100 for diagnosis, the imaging core can be used to measure a state inside a blood vessel.

The probe unit 101 is attached to the scanner and pull-back unit 102 in a freely detachable manner. A built-in motor of the scanner and pull-back unit 102 is driven so as to define axial motion and rotary motion inside a blood vessel around the axis of the imaging core which is interpolated into the probe unit 101. In addition, the scanner and pull-back unit 102 acquires reflected waves received by the ultrasound transmitting and receiving unit and the reflected light received by the light transmitting and receiving unit, thereby performing transmission to the operation control device 103.

The operation control device 103 can include a function of inputting various setting values when performing measurement and a function of processing data obtained through the measurement and displaying a tomographic image of the inside of a blood vessel.

In the operation control device 103, the reference numeral 111 indicates a main body control unit, which generates ultrasound data based on reflected waves obtained through the measurement, and performs processing of ultrasound line data generated based on the ultrasound data, thereby constructing an ultrasound tomographic image. Moreover, reflected light obtained through the measurement is caused to interfere with reference light obtained by separating light from a light source, thereby generating interference light data, and processing of optical line data generated based on the interference light data is performed, thereby constructing an optical tomographic image.

The reference numeral 111-1 indicates a printer and DVD recorder, which prints a processing result of the main body control unit 111 and stores the processing result as data. The reference numeral 112 indicates an operation panel, and a user inputs various setting values and instructions via the operation panel 112. The reference numeral 113 indicates an LCD monitor as a display device, which displays a tomographic image generated in the main body control unit 111.

Figure 2:
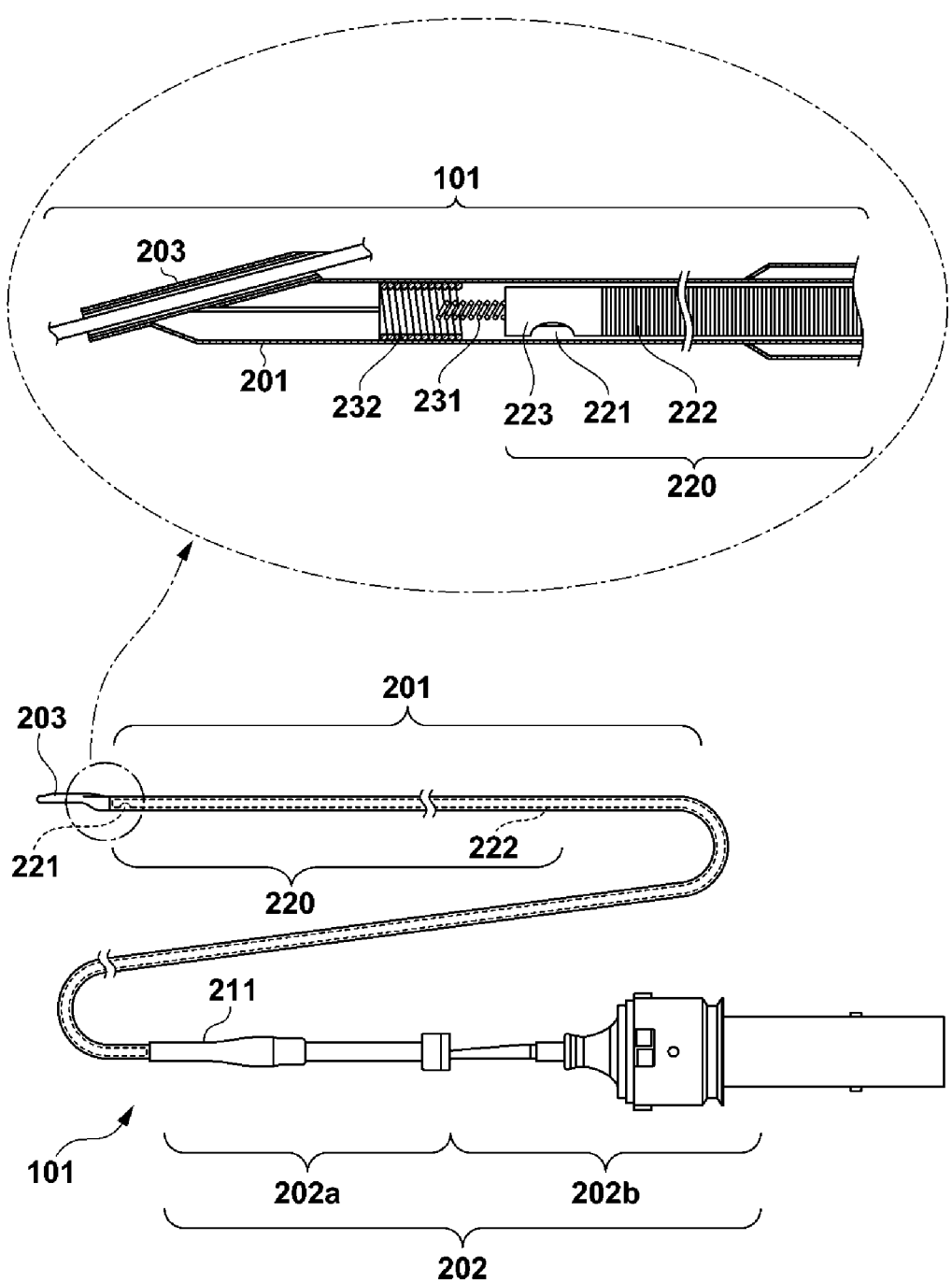
FIG. 2 is a diagram illustrating an overall constitution of a probe unit and a cross-sectional constitution of a distal end portion.

2. Overall Constitution of Probe Unit and Cross-Sectional Constitution of Distal End Portion Subsequently, an overall constitution of the probe unit 101 and a cross-sectional constitution of a distal end portion will be described with reference to FIG. 2. As illustrated in FIG. 2, the probe unit 101 is constituted to include an elongated catheter sheath 201, which is inserted into a blood vessel, and a connector portion 202, which is disposed on a hand side of a user to be operated by the user without being inserted into a blood vessel. A guide wire lumen tube 203 for constituting a guide wire lumen is provided at the distal end of the catheter sheath 201. The catheter sheath 201 forms a lumen, which continues from a portion connected to the guide wire lumen tube 203 to a portion connected to the connector portion 202.

Inside the lumen of the catheter sheath 201, an imaging core 220 including a transmitting and receiving unit 221 and a coiled drive shaft 222 is inserted through the catheter sheath 201 throughout substantially the overall length thereof. In the transmitting and receiving unit 221, the ultrasound transmitting and receiving unit for transmitting and receiving ultrasounds and the light transmitting and receiving unit for transmitting and receiving light are disposed. The drive shaft 222 can be internally provided with an electric signal cable and an optical fiber cable and transfers a rotary drive force for rotating the transmitting and receiving unit 221.

The connector portion 202 can include a sheath connector 202a which is constituted to be unified to a proximal end of the catheter sheath 201, and a drive shaft connector 202b which is constituted to rotatably fix the drive shaft 222 to a proximal end of the drive shaft 222.

A kink-proof protector 211 is provided at a boundary portion between the sheath connector 202a and the catheter sheath 201. Accordingly, predetermined rigidity is maintained so as to be able to prevent bending (kinking) occurring due to a rapid change of properties.

The proximal end of the drive shaft connector 202b is attached to the scanner and pull-back unit 102 in a freely detachable manner.

Subsequently, a cross-sectional constitution of the distal end portion of the probe unit 101 will be described. Inside the lumen of the catheter sheath 201, the imaging core 220 including a housing 223 and the drive shaft 222 is inserted throughout substantially the overall length thereof, thereby forming the probe unit 101. In the housing 223, there is provided the transmitting and receiving unit 221 in which the ultrasound transmitting and receiving unit for transmitting and receiving ultrasounds and the light transmitting and receiving unit for transmitting and receiving light are disposed. The drive shaft 222 transfers a rotary drive force for rotating the housing 223.

The drive shaft 222 can cause the transmitting and receiving unit 221 to perform the rotary motion and the axial motion with respect to the catheter sheath 201. The drive shaft 222 is constituted of a multiplex-multilayer bonding coil and the like formed with a metal wire, for example, stainless steel and the like having characteristics of being soft and favorably transferring rotations. Then, the electric signal cable and the optical fiber cable (the single mode optical fiber cable) are arranged inside of the drive shaft 222.

The housing 223 is a metallic pipe having a short cylindrical shape in which a notch portion is partially provided. The housing 223 is molded by performing carving from a metal ingot and metal powder injection molding (MIM). In addition, a short coiled elastic member 231 is provided on the distal end side of the housing 223.

The elastic member 231 is formed with a coiled stainless steel wire. Since the elastic member 231 is disposed on the distal end side, the imaging core 220 is prevented from being caught inside the catheter sheath 201 when moving forward and rearward.

The reference numeral 232 indicates a reinforcement coil which is provided for the purpose of helping prevent sudden bending at the distal end portion of the catheter sheath 201.

The guide wire lumen tube 203 has a lumen for guide wire allowing a guide wire to be inserted. The guide wire lumen tube 203 is used for receiving the guide wire, which has been inserted into a blood vessel in advance, and causing the guide wire to guide the catheter sheath 201 to a target lesion.

3. Cross-Sectional Constitution of Imaging Core

Subsequently, a cross-sectional constitution of the imaging core 220 and a disposition of the ultrasound transmitting and receiving unit and the light transmitting and receiving unit will be described. FIGS. 3A-3C are diagrams illustrating the cross-sectional constitution of the imaging core and the disposition of the ultrasound transmitting and receiving unit and the light transmitting and receiving unit.

As illustrated in FIG. 3A, the transmitting and receiving unit 221 which is arranged inside the housing 223 can include an ultrasound transmitting and receiving unit 310 and a light transmitting and receiving unit 320. The ultrasound transmitting and receiving unit 310 and the light transmitting and receiving unit 320 are disposed on a rotary center axis (on a dot and dash line in FIG. 3a) of the drive shaft 222 along the axial direction while being separated from each other by a distance L.

Of these units, the ultrasound transmitting and receiving unit 310 is disposed on the distal end side of the probe unit 101, and the light transmitting and receiving unit 320 is disposed on the proximal end side of the probe unit 101.

The ultrasound transmitting and receiving unit 310 and the light transmitting and receiving unit 320 are attached to the inside of the housing 223 so as to cause each of an ultrasound transmitting and receiving direction (an elevation angle direction) of the ultrasound transmitting and receiving unit 310 and a light transmitting and receiving direction (an elevation angle direction) of the light transmitting and receiving unit 320 to be substantially 90° with respect to the axial direction of the drive shaft 222. It is desirable to perform attachment while causing each of the transmitting and receiving directions to be slightly misaligned from 90° so as not to receive reflection from the inner surface of the lumen in the catheter sheath 201.

Inside the drive shaft 222, an electrical signal cable 311 which is connected to the ultrasound transmitting and receiving unit 310, and an optical fiber cable 321 which is connected to the light transmitting and receiving unit 320 are disposed. IN accordance with an exemplary embodiment, the electrical signal cable 311 can be wound around the optical fiber cable 321 in a spiral manner.

FIG. 3B is a cross-sectional view when being cut on a plane, which is substantially orthogonal to the rotary center axis at an ultrasound transmitting and receiving position. As illustrated in FIG. 3B, when the downward direction of the sheet is considered as zero degrees, the ultrasound transmitting and receiving direction (the circumferential direction (also referred to as the azimuth angle direction)) of the ultrasound transmitting and receiving unit 310 becomes 8 degrees.

FIG. 3C is a cross-sectional view when being cut on a plane, which is substantially orthogonal to the rotary center axis at the light transmitting and receiving position. As illustrated in FIG. 3C, when the downward direction of the sheet is considered as zero degrees, the light transmitting and receiving direction (the circumferential direction) of the light transmitting and receiving unit 320 becomes zero degrees. In other words, the ultrasound transmitting and receiving unit 310 and the light transmitting and receiving unit 320 are disposed so as to cause the ultrasound transmitting and receiving direction (the circumferential direction) of the ultrasound transmitting and receiving unit 310 and the light transmitting and receiving direction (the circumferential direction) of the light transmitting and receiving unit 320 to be mutually misaligned by an angular difference of 8 degrees.

4. Functional Constitution of Imaging Apparatus for Diagnosis

Figure 4:
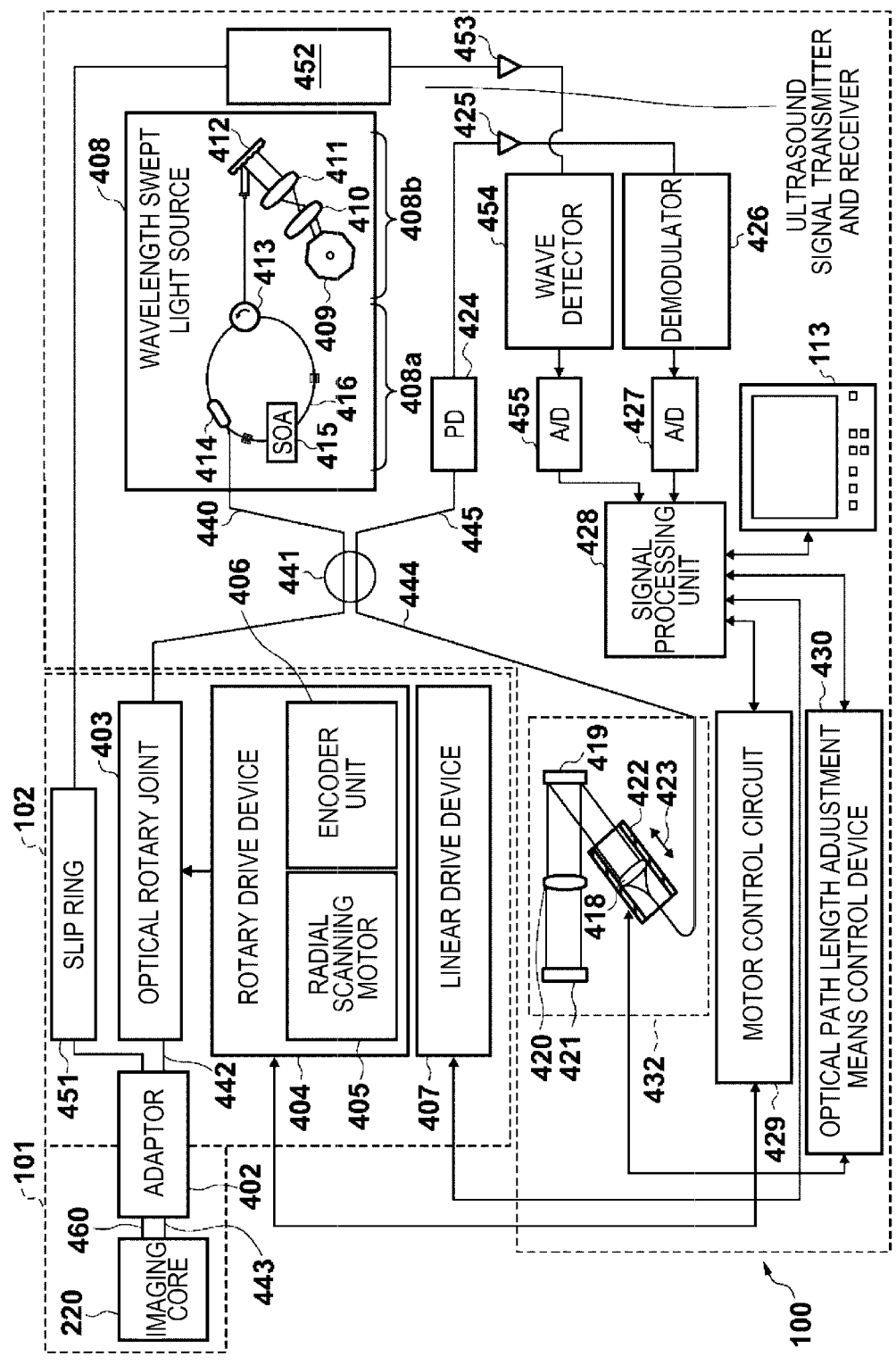
FIG. 4 is a diagram illustrating a functional constitution of the imaging apparatus for diagnosis.

Subsequently, a functional constitution of the imaging apparatus 100 for diagnosis will be described. FIG. 4 is a diagram illustrating the functional constitution of the imaging apparatus 100 for diagnosis in which the function of the IVUS and the function of the OCT (herein, a swept source OCT as an example) are combined together. An imaging apparatus for diagnosis in which the function of the IVUS and a function of different OCT are combined together also has a similar functional constitution, thereby omitting the description thereof herein.

(1) Function of IVUS

The imaging core 220 internally can include the ultrasound transmitting and receiving unit 310 at the distal end thereof. The ultrasound transmitting and receiving unit 310 transmits ultrasounds to a biological tissue in a blood vessel based on pulse waves transmitted from an ultrasound signal transmitter and receiver 452, and receives reflected waves thereof, thereby transmitting the reflected waves to the ultrasound signal transmitter and receiver 452 as an ultrasound signal via an adaptor 402 and a slip ring 451.

In the scanner and pull-back unit 102, a rotary drive portion side of the slip ring 451 is rotatively driven by a radial scanning motor 405 of a rotary drive device 404. In this manner, the rotary motion of the imaging core 220 is defined. A rotary angle of the radial scanning motor 405 is detected by an encoder unit 406. Moreover, the scanner and pull-back unit 102 can include a linear drive device 407 and defines the axial motion of the imaging core 220 based on a signal from a signal processing unit 428.

The ultrasound signal transmitter and receiver 452 can include a transmission wave circuit and a reception wave circuit (not illustrated). The transmission wave circuit transmits pulse waves to the ultrasound transmitting and receiving unit 310 inside the imaging core 220 based on a control signal transmitted from the signal processing unit 428.

In addition, the reception wave circuit receives an ultrasound signal from the ultrasound transmitting and receiving unit 310 inside the imaging core 220. The received ultrasound signal is amplified by an amplifier 453, and then, the amplified signal is input to a wave detector 454 so as to be subjected to wave detection.

Moreover, in an A/D converter 455, an ultrasound signal output from the wave detector 454 is sampled at 30.6 MHz at as many as 200 points, thereby generating digital data for one line ("the ultrasound line data" which is digital data indicating strength of the signals reflected by the ultrasound transmitting and receiving unit 310 from each of the positions in the transmitting and receiving directions of ultrasounds). Herein, the frequency can be set to, for example, 30.6 MHz on the premise that the sampling is performed at 200 points with respect to the depth of, for example, 5 mm when the propagation velocity of the ultrasounds in a blood vessel tissue is considered to be, for example, 1,530 m/sec. Therefore, the sampling frequency is not particularly limited thereto.

The ultrasound line data generated by the A/D converter 455 in a line unit is input to the signal processing unit 428. In the signal processing unit 428, the ultrasound line data is converted into a gray scale so as to construct an ultrasound tomographic image at each of the positions in a blood vessel, thereby outputting the ultrasound tomographic image to the LCD monitor 113 at a predetermined frame rate.

The signal processing unit 428 is connected to a motor control circuit 429 and receives a video synchronization signal of the motor control circuit 429. Then, in the signal processing unit 428, the ultrasound tomographic image is constructed by being synchronized with the received video synchronization signal. In addition, the video synchronization signal of the motor control circuit 429 is also transmitted to the rotary drive device 404. Then, the rotary drive device 404 outputs a drive signal which is synchronized with the received video synchronization signal.

(2) Function of Swept Source OCT

Subsequently, a functional constitution of the swept source OCT will be described with reference to the same diagram. The reference numeral 408 indicates a wavelength swept light source (swept laser), which is a type of an extended-cavity laser constituted of an optical fiber 416 coupled with a semiconductor optical amplifier 415 (SOA) in a ring shape, and a polygon scanning filter (408b).

Light output from the SOA 415 passes through the optical fiber 416 and enters the polygon scanning filter 408b. The light is subjected to wavelength selection herein, is amplified by the SOA 415, and is lastly output from a coupler 414.

In the polygon scanning filter 408b, the wavelength is selected through a combination of a diffraction grating 412 which diffracts light, and a polygon mirror 409. In accordance with an exemplary embodiment, for example, the light diffracted by the diffraction grating 412 is concentrated on a surface of the polygon mirror 409 by using two lenses (410 and 411). Accordingly, only the light having a wavelength orthogonal to the polygon mirror 409 returns to the same optical path, thereby being output from the polygon scanning filter 408b. In accordance with an exemplary embodiment, for example, time sweeping of a wavelength can be performed by rotating the polygon mirror 409.

In the polygon mirror 409, for example, a 32-hedron mirror is used and the number of rotations is approximately 50,000 rpm. In accordance with an exemplary embodiment, high-speed and high-output wavelength sweeping through the wavelength swept source method can be performed in which the polygon mirror 409 and the diffraction grating 412 are combined together.

Light of the wavelength swept light source 408 output from the coupler 414 is incident on one end of a first single mode fiber 440, thereby being transferred to the distal end side of the first single mode fiber 440. The first single mode fiber 440 is optically coupled to a second single mode fiber 445 and a third single mode fiber 444 in a photo coupler unit 441 in the middle therebetween.

On the distal end side from the photo coupler unit 441 of the first single mode fiber 440, an optical rotary joint (an optical coupling portion) 403 which connects a non-rotary portion (fixed portion) and a rotary portion (rotary drive portion) with each other and transfers light is provided inside the rotary drive device 404.

Moreover, on a distal end side of a fourth single mode fiber 442 in the optical rotary joint (the optical coupling portion) 403, a fifth single mode fiber 443 of the probe unit 101 is connected thereto via the adaptor 402 in a freely detachable manner. Accordingly, light from the wavelength swept light source 408 is transferred to the rotatably driven fifth single mode fiber 443, which is inserted through the inside of the imaging core 220.

Irradiation of the transferred light in rotary motion and axial motion is performed with respect to a biological tissue in a blood vessel from the light transmitting and receiving unit 320 of the imaging core 220. A portion of the reflected light scattering on a surface or inside a biological tissue is collected by the light transmitting and receiving unit 320 of the imaging core 220, and returns to the first single mode fiber 440 side via the optical path in reverse. Moreover, the portion of the reflected light moves to the second single mode fiber 445 side by the photo coupler unit 441 and is emitted from one end of the second single mode fiber 445. Thereafter, the portion of the reflected light is received by a photo detector (for example, a photo diode 424).

The rotary drive portion side of the optical rotary joint 403 is rotatively driven by the radial scanning motor 405 of the rotary drive device 404.

In accordance with an exemplary embodiment, an optical path length variable mechanism 432 for performing fine adjustment of the length of the optical path of the reference light is provided at the distal end on a side opposite to the photo coupler unit 441 of the third single mode fiber 444.

The optical path length variable mechanism 432 can include optical path length changing means for changing the length of the optical path corresponding to a fluctuation in the length of each probe unit 101 so as to be able to absorb the fluctuation in the length thereof when the probe unit 101 is replaced and used.

The third single mode fiber 444 and a collimating lens 418 are provided on a one-axis stage 422 which is movable in the optical-axis direction (the arrow 423) thereof, thereby forming the optical path length changing means.

In accordance with an exemplary embodiment, for example, the one-axis stage 422 functions as the optical path length changing means having a variable range of the optical path length as wide as the fluctuation in the length of the optical path of the probe unit 101 when the probe unit 101 is replaced. Moreover, the one-axis stage 422 also can include a function as adjustment means for adjusting an offset. For example, even when the distal end of the probe unit 101 is not in close contact with a surface of a biological tissue, a state can be set where the reference light is interfered with the reflected light from the surface position of the biological tissue by performing fine changing of the length of the optical path through the one-axis stage.

The length of the optical path is subjected to fine adjustment through the one-axis stage 422, and light reflected by the mirror 421 via a grating 419 and a lens 420 is mixed with light obtained from the first single mode fiber 440 side in the photo coupler unit 441 which is provided in the middle of the third single mode fiber 444, thereby being received by the photo diode 424.

The interference light received by the photo diode 424 as described above is subjected to photoelectric conversion, thereby being input to a demodulator 426 after being amplified by the amplifier 425. The demodulator 426 performs demodulation processing of extracting only a signal portion of the interference light, and an output thereof is input to an A/D converter 427 as an interference light signal.

In the A/D converter 427, the interference light signal is sampled at, for example, 180 MHz at as many as 2,048 points, for example, thereby generating digital data (interference light data) for one line. The sampling frequency can be set, for example, to 180 MHz on the premise that approximately 90% of a periodical cycle (12.5 μsec) of the wavelength sweeping is extracted as digital data at 2,048 points when a repetition frequency of the wavelength sweeping is set to 80 kHz. However, the sampling frequency is not particularly limited thereto.

The interference light data generated by the A/D converter 427 in a line unit is input to the signal processing unit 428. The signal processing unit 428 generates data ("the optical line data" which is data indicating strength of light reflected by the light transmitting and receiving unit 320 from each of the positions in the transmitting and receiving directions of light) in a depth direction by causing the interference light data to be subjected to frequency resolution through fast fourier transform (FFT). Then, the generated data is subjected to coordinate conversion so as to construct an optical tomographic image at each position in a blood vessel, thereby outputting the constructed image to the LCD monitor 113 at a predetermined frame rate.

Furthermore, the signal processing unit 428 is further connected to an optical path length adjustment means control device 430 and controls a position of the one-axis stage 422 via the optical path length adjustment means control device 430.

5. Description of Signal Processing Unit 428

Figure 5:
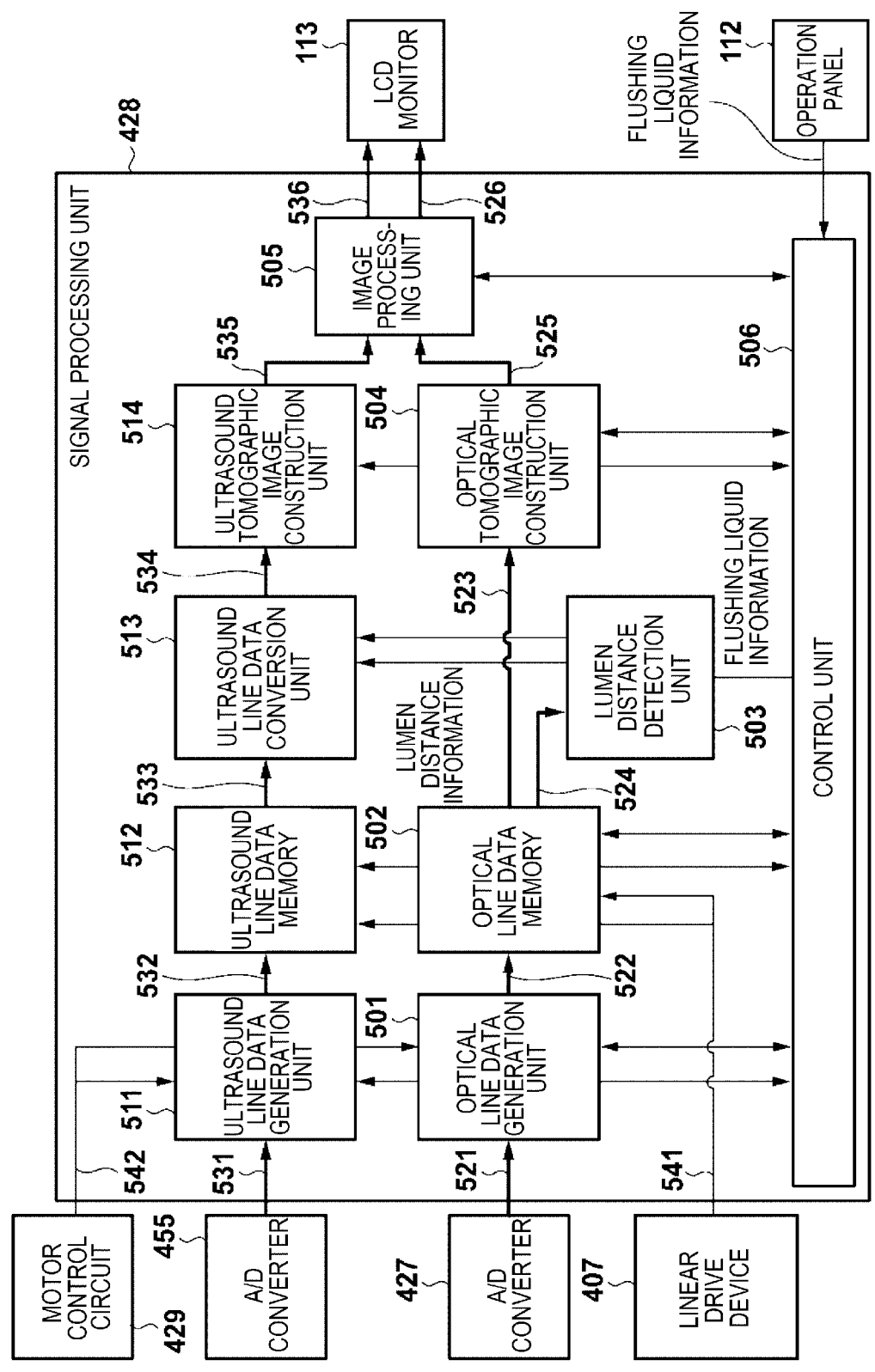
FIG. 5 is a diagram illustrating a functional constitution of a signal processing unit of the imaging apparatus for diagnosis.

Subsequently, a functional constitution of the signal processing unit 428 of the imaging apparatus 100 for diagnosis will be described. FIG. 5 is a diagram illustrating a functional constitution of the signal processing unit 428 of the imaging apparatus 100 for diagnosis and related functional blocks thereof. The functional constitution illustrated in FIG. 5 may be realized by using exclusive hardware or may be partially realized through software (for example, by causing a computer to execute a program for realizing the function).

As illustrated in FIG. 5, the interference light data 521 generated by the A/D converter 427 is processed so as to have 512 lines per one rotation in an optical line data generation unit 501 inside the signal processing unit 428, by using a signal of the encoder unit 406 of the radial scanning motor 405 output from the motor control circuit 429.

Optical line data 522 output by the optical line data generation unit 501 is stored in an optical line data memory 502 by the volume for each rotation (one frame) based on an instruction from a control unit 506. In this case, the control unit 506 counts pulse signals 541, which are output by a movement amount detector of the linear drive device 407. When storing the optical line data 522 in the optical line data memory 502, each of the counted values at the time of generating the optical line data 522 is caused to correspond thereto.

Optical line data 523 which is stored so as to correspond to the counted value is input to an optical tomographic image construction unit 504 and is subjected to RO conversion after various types of processing (line addition averaging processing, filtering processing, and the like) are performed, thereby being sequentially output as optical tomographic images 525.

In addition, optical line data 524 stored so as to correspond to the counted value is also input to a lumen distance calculation unit 503. In the lumen distance calculation unit 503, a position of an outer surface of the sheath and a position of the lumen can be individually detected based on each item of the optical line data, thereby calculating a lumen distance d from the position of the outer surface of the sheath to the position of the lumen. The calculated lumen distance d is input to an ultrasound line data conversion unit 513 as lumen distance information.

An optical tomographic image 525 output from the optical tomographic image construction unit 504 is subjected to image processing by an image processing unit 505 so as to be displayed on the LCD monitor 113, and then, can be output to the LCD monitor 113 as an optical tomographic image 526.

In accordance with an exemplary embodiment, ultrasound data 531 generated by the A/D converter 455 is processed so as to have 512 lines per one rotation in an ultrasound line data generation unit 511 inside the signal processing unit 428, using a signal of the encoder unit 406 of the radial scanning motor 405 which is output from the motor control circuit 429. The ultrasound line data generated at this time is generated by using a propagation velocity $V_0$ of ultrasounds in a blood vessel tissue.

Ultrasound line data 532 output by the ultrasound line data generation unit 511 is stored in an ultrasound line data memory 512 by the volume for each rotation (one frame) based on an instruction from the control unit 506. In this case, the control unit 506 counts pulse signals 541, which can be output by the movement amount detector of the linear drive device 407. When storing the ultrasound line data 532 in the line data memory 512, each of the counted values at the time of generating the ultrasound line data 532 is caused to correspond thereto (the corresponding counted values at this time are the counted values in which the above-described angular difference θ and the distance L between the ultrasound transmitting and receiving unit 310 and the light transmitting and receiving unit 320 are considered. In accordance with an exemplary embodiment, if the count values are the same, the ultrasound line data and the optical line data are considered to be indicating the same position in a blood vessel).

Ultrasound line data 533 which is stored so as to correspond to the counted value is input to the ultrasound line data conversion unit 513, scale conversion processing is executed based on information received by the control unit 506 related to a flushing liquid (a medium used when performing a flushing operation) and lumen distance information (Td) received by the lumen distance calculation unit 503 (the corresponding ultrasound propagation velocities are stored in the control unit 506 as information related to the flushing liquid by being classified for each type of the flushing liquid in advance. The ultrasound propagation velocities in a blood vessel tissue are also stored together as the default thereof).

The scale conversion processing is executed while targeting the range within the lumen distance Td from the position of the outer surface of the sheath among the items of the ultrasound line data (will be described later in detail). In addition, information of the flushing liquid is input by a user via the operation panel 112.

Ultrasound line data 534 which is subjected to scale conversion processing by the ultrasound line data conversion unit 513 is input to an ultrasound tomographic image construction unit 514. Then, the ultrasound line data 534 is subjected to Re conversion after various types of processing (line addition averaging processing, filtering processing, and the like) are performed by the ultrasound tomographic image construction unit 514 based on an instruction from the control unit 506, thereby being sequentially output as ultrasound tomographic images 535.

Moreover, the ultrasound tomographic image 535 is subjected to image processing by the image processing unit 505 so as to be displayed on the LCD monitor 113, and then, is output to the LCD monitor 113 as an ultrasound tomographic image 536.

6. Operation of Imaging Core 220

Subsequently, a relationship between an operation of the imaging core 220 in a blood vessel and line data (the ultrasound line data and the optical line data) acquired by the operation of the imaging core 220 will be described.

Figure 6:
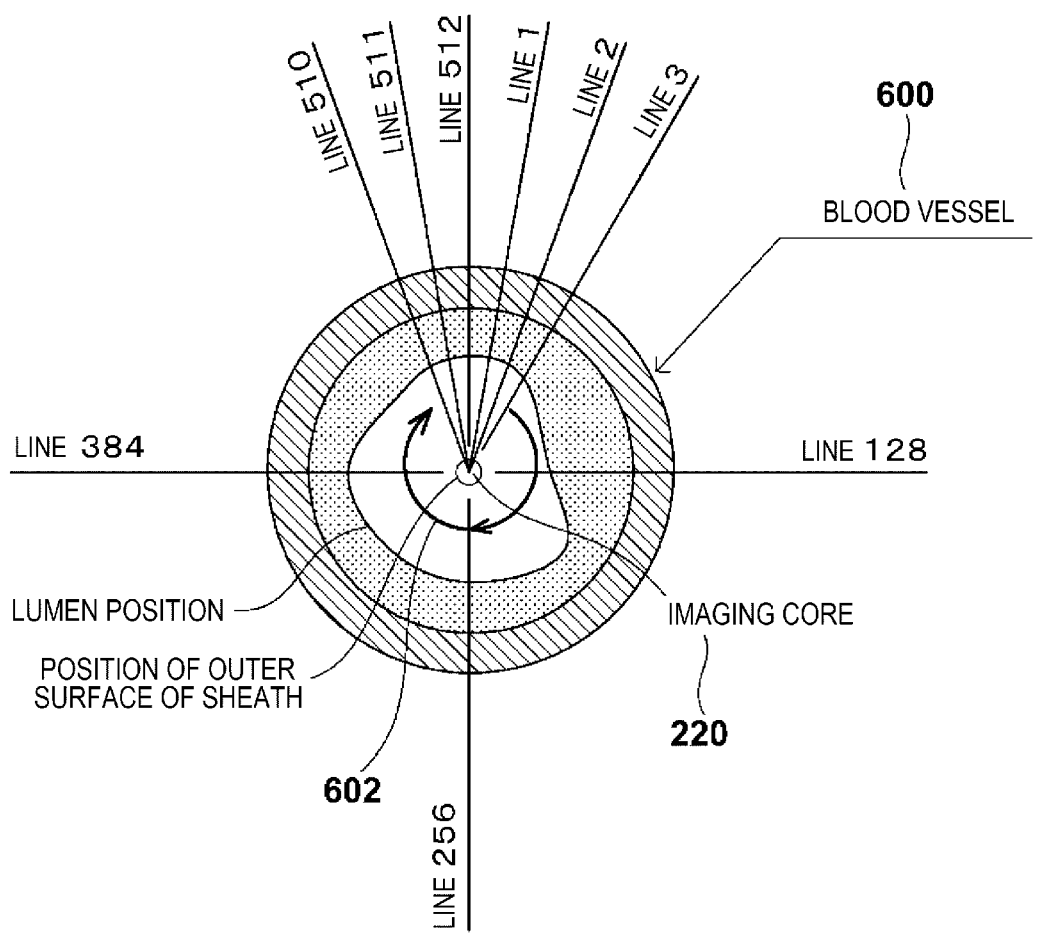
FIG. 6 is a diagram for illustrating a data structure of a generated tomographic image.

FIG. 6 illustrates a state where the imaging core 220 inserted through the inside of a blood vessel 600 is seen in a cross-sectional direction of the blood vessel 600. When processing of constructing a tomographic image starts in the above-described state, the flushing liquid flows on the outer side of the catheter sheath in which the imaging core 220 is interpolated, that is, the inner side of the position of the lumen (in accordance with an exemplary embodiment, between the position of the outer surface of the sheath and the position of the lumen), and the radial scanning motor 405 rotates the imaging core 220 in a direction of an arrow 602.

In this case, in the ultrasound transmitting and receiving unit 310, transmission/reception of ultrasounds is performed at each of the rotary angles. The lines 1, 2, and so on to 512 indicate transmitting and receiving directions of ultrasounds at each of the rotary angles. In the imaging apparatus 100 for diagnosis according to the present embodiment, while the ultrasound transmitting and receiving unit 310 turns 360 degrees in the blood vessel 600, transmission/reception of ultrasounds is intermittently performed 512 times. Accordingly, 512 items of the ultrasound line data can be generated.

In accordance with an exemplary embodiment, in the light transmitting and receiving unit 320 as well, transmission/reception of light is performed at each of the rotary angles. While the light transmitting and receiving unit 320 turns 360 degrees in the blood vessel 600, transmission/reception of light is continuously performed 512 times. Accordingly, 512 items of the optical line data are generated.

7. Overview of Scale Conversion Processing of Ultrasound Line Data

Figure 7A:
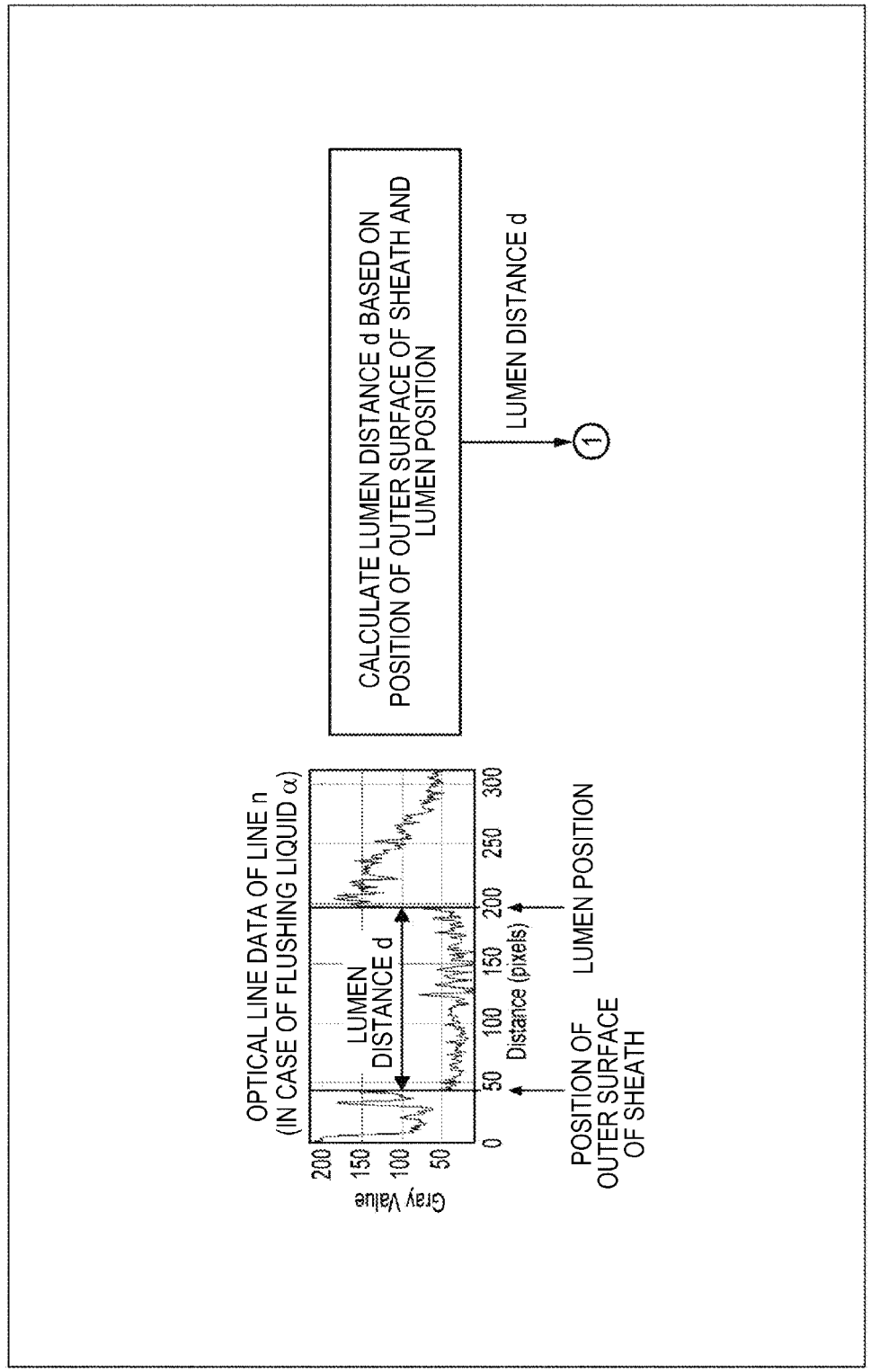
FIG. 7A is a diagram for illustrating an overview of ultrasound line data conversion processing.
Figure 7B:
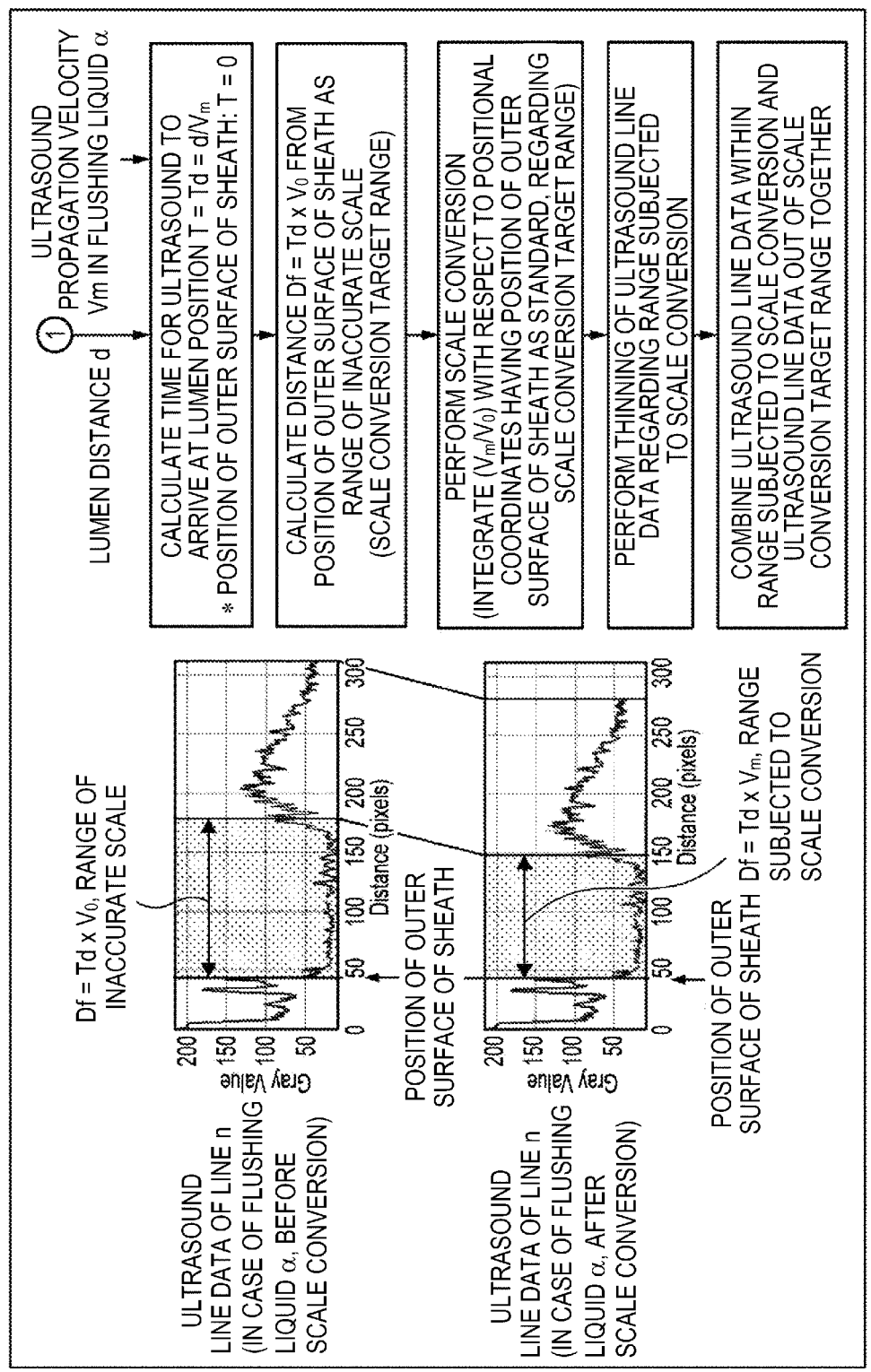
FIG. 7B is a diagram for illustrating another overview of the ultrasound line data conversion processing.

Subsequently, the overview of scale conversion processing of the ultrasound line data will be described with reference to FIGS. 7A and 7B. FIGS. 7A and 7B are diagrams for illustrating the overview of scale conversion processing of the ultrasound line data. FIG. 7A illustrates lumen distance calculation processing performed by the lumen distance calculation unit 503, and FIG. 7B illustrates scale conversion processing performed by the ultrasound line data conversion unit 513.

As illustrated in FIG. 7A, the lumen distance calculation unit 503 detects each of the position of the outer surface of the sheath and the position of the lumen based on the optical line data of the line n (n is an arbitrary integer from 1 to 512) stored in the optical line data memory 502. Moreover, the lumen distance calculation unit 503 calculates the distance from the position of the outer surface of the sheath to the position of the lumen (referred to as "the lumen distance d")

based on the position of the outer surface of the sheath and the position of the lumen, which have been detected. The lumen distance d calculated by the lumen distance calculation unit 503 is input to the ultrasound line data conversion unit 513.

Here, as illustrated in FIG. 7B, in the ultrasound line data conversion unit 513, the control unit 506 receives the value of a propagation velocity $V_m$ of ultrasounds in the flushing liquid α which is used in the flushing operation.

In the ultrasound line data conversion unit 513, a time Td ($=d/V_m$) taken from the position of the outer surface of the sheath to the position of the lumen is calculated in a case where ultrasounds are propagated in the flushing liquid α (here, the position of the outer surface of the sheath is detected based on the ultrasound line data, and a time T which is the time when ultrasounds pass through the position of the outer surface of the sheath is considered to be "0").

Since the time Td calculated in this case is the time when ultrasounds are propagated in the flushing liquid α, the accurate position of the lumen in the ultrasound line data can be specified by integrating the propagation velocity $V_m$ of ultrasounds in the flushing liquid α.

However, when generating the ultrasound line data in the present embodiment, the propagation velocity $V_0$ of ultrasounds in a blood vessel tissue is used as the propagation velocity of the ultrasounds. Therefore, an error of the scale is included in a range within a distance $Df=Td \times V_0$ from the position of the outer surface of the sheath in every ultrasound line data which is input to the ultrasound line data conversion unit 513. In contrast, since a position away from the position of the outer surface of the sheath farther than the distance Df is a blood vessel tissue (that is, since there is no flushing liquid), it is suitable to use the value $V_0$ as the propagation velocity of the ultrasounds (refer to the upper side of the sheet in FIG. 7B).

Therefore, the ultrasound line data conversion unit 513 performs scale conversion processing with respect to the range within the distance Df from the position of the outer surface of the sheath, that is, a range in which the scale is inaccurate, as the target range for scale conversion. Specifically, a value of $V_m/V_0$ is integrated with respect to each of positional coordinates (positional information of each position) from the outer surface of the sheath regarding the ultrasound line data within the target range.

Accordingly, each of the positional coordinates in the target range (in the range within the distance Df from the position of the outer surface of the sheath) subjected to scale conversion is converted into each of the positional coordinates in a range within a distance Df' ($=Td \times V_m$) from the position of the outer surface of the sheath. In the example of FIG. 7B, since $V_m < V_0$, compared to the distance from the position of the outer surface of the sheath to the position of the lumen before scale conversion is performed, the distance from the outer surface of the sheath to the position of the lumen after scale conversion is performed becomes short (the distance becomes short as much as the ratio between the values $V_m$ and $V_0$). Therefore, the ultrasound line data within the range is thinned out.

Since there is no need to perform scale conversion processing with respect to the ultrasound line data for the position away from the position of the outer surface of the sheath farther than the distance Df (a blood vessel tissue on the outer side from the position of the lumen), the data is subjected to a parallel movement as it is and is combined therewith following after the ultrasound line data which has been subjected to scale conversion processing. As a result, the ultrasound line data after scale conversion is generated (refer to the lower side of the sheet in FIG. 7B).

8. Flow of Ultrasound Line Data Conversion Processing

Figure 8:
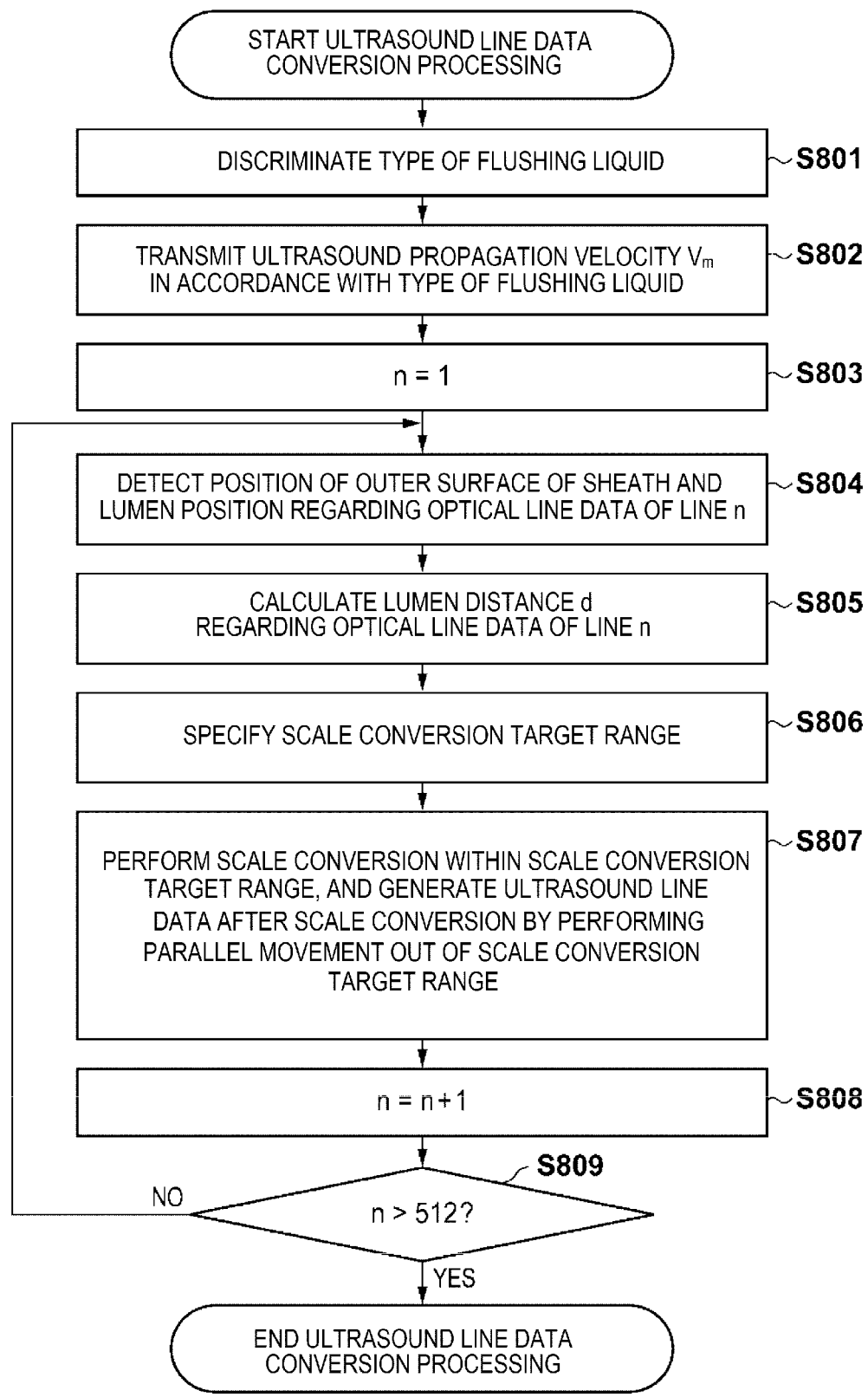
FIG. 8 is a flow chart illustrating a flow of the ultrasound line data conversion processing.

Subsequently, a flow of ultrasound line data conversion processing performed by the signal processing unit 428 will be described. FIG. 8 is a flow chart illustrating a flow of ultrasound line data conversion processing for one frame, performed by the signal processing unit 428.

As illustrated in FIG. 8, in Step S801, discrimination of the type of the flushing liquid is performed, and in Step S802, the value of the ultrasound propagation velocity $V_m$ in accordance with the type of the flushing liquid discriminated in Step S801 is transmitted to the ultrasound line data conversion unit 513 by the control unit 506.

In Step S803, the numerical value "1" is input to the counter n, and in Step S804, the position of the outer surface of the sheath and the position of the lumen are detected regarding the optical line data of the line n (here, the line 1). Moreover, in Step S805, the lumen distance d in the optical line data of the line n is calculated based on the position of the outer surface of the sheath and the position of the lumen.

In Step S806, the target range of scale conversion is specified based on the value ($V_0$) which can be set in advance as the ultrasound propagation velocity in a blood vessel tissue, the ultrasound propagation velocity $V_m$ transmitted in Step S802, and the lumen distance d acquired in Step S805. Specifically, the range within the distance Df ($=(d/V_m) \times V_0$) from the position of the outer surface of the sheath detected in the ultrasound line data is specified as the target range of scale conversion.

In Step S807, scale conversion processing is performed regarding the ultrasound line data within the target range of scale conversion specified in Step S806. Then, after performing a parallel movement of each of the positional coordinates for the ultrasound line data out of the target range of scale conversion, the ultrasound line data after scale conversion is generated by being combined with the ultrasound line data within the target range of scale conversion.

In Step S808, an increment of the counter n is performed, and in Step S809, it is determined whether or not the counter n is greater than 512. When it is determined that the counter n is equal to or less than 512 in Step S809, the processing returns to Step S804, and scale conversion processing is performed with respect to 512 items of the ultrasound line data forming one frame.

Meanwhile, when scale conversion processing is completed with respect to the 512 items of the ultrasound line data forming one frame, processing ends.

As is clear from the above description, in the imaging apparatus 100 for diagnosis according to the present embodiment, it is constituted to arrange the ultrasound line data conversion unit so as to perform scale conversion processing for each item of the ultrasound line data.

It is constituted to use the ultrasound propagation velocity in accordance with the type of the flushing liquid when performing scale conversion processing.

It is constituted to specify the target range of scale conversion by using the lumen distance which is calculated based on the optical line data.

It is constituted to perform scale conversion processing within the specified target range of scale conversion based on the ratio between the ultrasound propagation velocity in a blood vessel tissue and the ultrasound propagation velocity in accordance with the type of the flushing liquid, which can be used when generating the ultrasound line data before scale conversion.

Accordingly, an error of the scale of an ultrasound tomographic image regardless of the type of the flushing liquid can be reduced.

In the first embodiment, it is constituted to perform scale conversion processing regarding the ultrasound line data within a range corresponding to a region in which a flushing liquid flows, after the ultrasound line data is generated by using the ultrasound propagation velocity $V_0$ in a blood vessel tissue. However, the present disclosure is not limited thereto.

For example, it may be constituted to perform scale conversion processing regarding the ultrasound line data within a range of a blood vessel tissue, after the ultrasound line data is generated by using the ultrasound propagation velocity $V_m$ in the flushing liquid. Hereinafter, the present embodiment will be described in detail.

1. Overview of Scale Conversion Processing of Ultrasound Line Data

Figure 9:
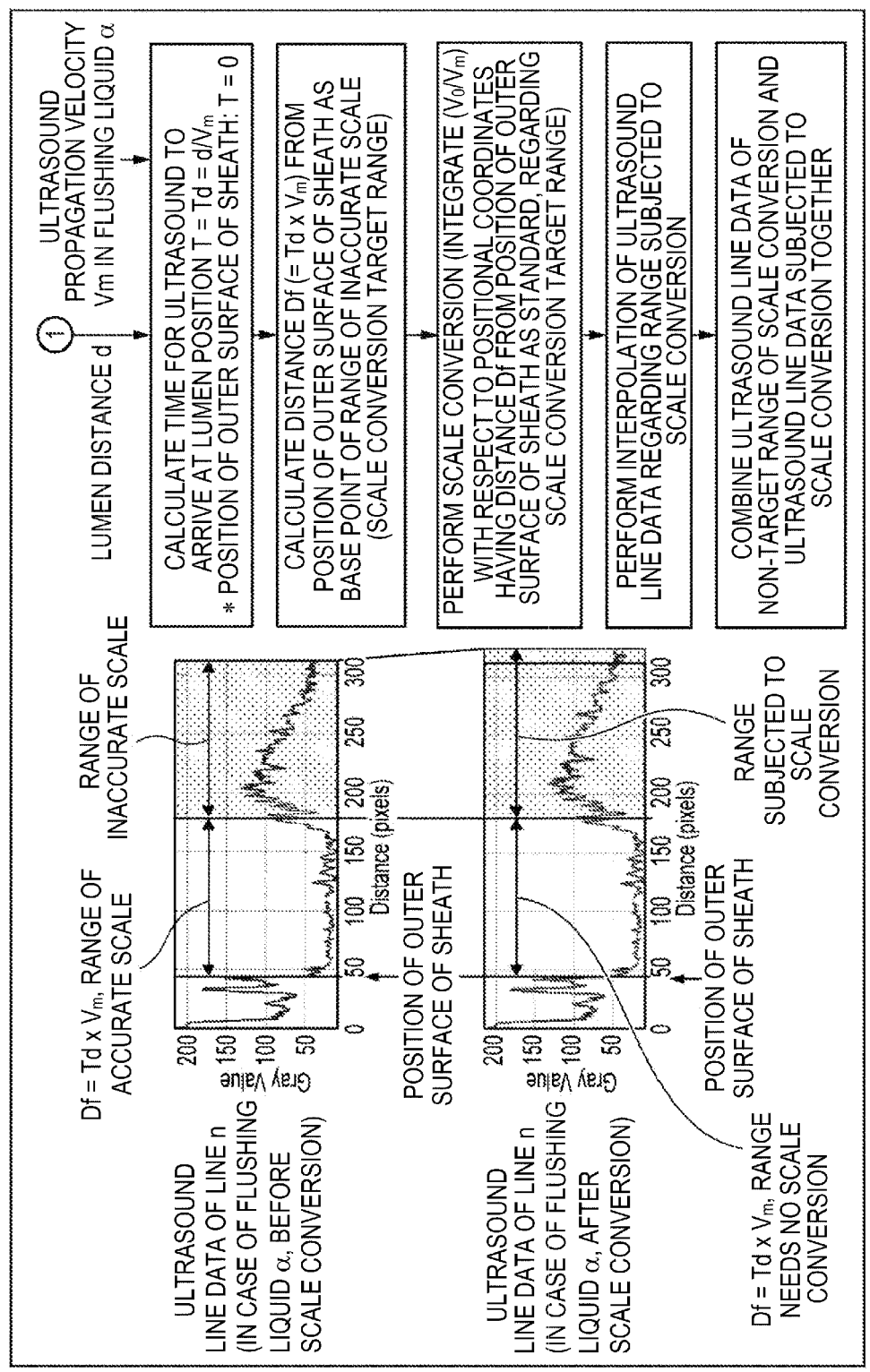
FIG. 9 is a diagram for illustrating further another overview of the ultrasound line data conversion processing.

First, an overview of scale conversion processing of the ultrasound line data according to the present embodiment will be described with reference to FIGS. 7A and 9. FIGS. 7A and 9 are diagrams for illustrating the overview of scale conversion processing of the ultrasound line data. As described above, FIG. 7A illustrates lumen distance calculation processing performed by the lumen distance calculation unit 503, and FIG. 9 illustrates scale conversion processing performed by the ultrasound line data conversion unit 513. Since FIG. 7A has already been described in the first embodiment, the descriptions thereof will be omitted herein.

As illustrated in FIG. 9, in the ultrasound line data conversion unit 513, the control unit 506 receives the value of the propagation velocity $V_m$ of ultrasounds in the flushing liquid α which is used when performing flushing.

In the ultrasound line data conversion unit 513, the time Td taken from the position of the outer surface of the sheath to the position of the lumen is calculated in a case where ultrasounds are propagated in the flushing liquid α (here, the position of the outer surface of the sheath is detected based on the ultrasound line data, and the time T which is the time when ultrasounds pass through the position of the outer surface of the sheath is considered to be "0").

Since the time Td calculated in this case is the time when ultrasounds are propagated in the flushing liquid α, the accurate position of the lumen (a position within the distance Df=Td×Vm from the position of the outer surface of the sheath, that is, d) in the ultrasound line data can be specified, if the propagation velocity $V_m$ of ultrasounds in the flushing liquid α is integrated.

In the present embodiment, since the ultrasound line data is generated based on the propagation velocity $V_m$ of ultrasounds in the flushing liquid α, the range within the distance Df from the position of the outer surface of the sheath in the ultrasound line data is a range in which the propagation velocity of ultrasounds is not affected (that is, a non-target range of scale conversion).

Meanwhile, the ultrasound line data at the position away from the position of the outer surface of the sheath farther than the distance Df (a blood vessel tissue on the outer side from the position of the lumen) among the items of the ultrasound line data is not generated by using the propagation velocity $V_0$ in a blood vessel tissue. Therefore, an error of the scale is included in a range away from the position of the outer surface of the sheath farther than the distance Df=Td×Vm in every ultrasound line data which is input to the ultrasound line data conversion unit 513 (refer to the upper side of the sheet in FIG. 9).

Therefore, scale conversion processing is performed with respect to the range away from the position of the outer surface of the sheath farther than the distance Df, for example, a range in which the scale is inaccurate, as the target range for scale conversion. Specifically, the value of $V_0/V_m$ is integrated with respect to each of the positional coordinates having the position of the lumen (the position away from the outer surface of the sheath by the distance Df) as the standard, regarding the ultrasound line data within the target range.

Accordingly, the positional coordinates at each position in the target range (in the range away from the position of the outer surface of the sheath farther than the distance Df) subjected to scale conversion is converted. In the example of FIG. 9, since $V_m<V_0$, compared to the range before scale conversion is performed, the range after scale conversion is performed becomes wide (the range becomes wide as much as the ratio between the values $V_m$ and $V_0$). Therefore, the ultrasound line data within the range is interpolated.

Since scale conversion is not performed with respect to the ultrasound line data within the distance Df from the position of the outer surface of the sheath, the ultrasound line data within the range subjected to scale conversion is combined therewith as it is. As a result, the ultrasound line data after scale conversion is generated (refer to the lower side of the sheet in FIG. 9).

2. Flow of Ultrasound Line Data Conversion Processing

Figure 10:
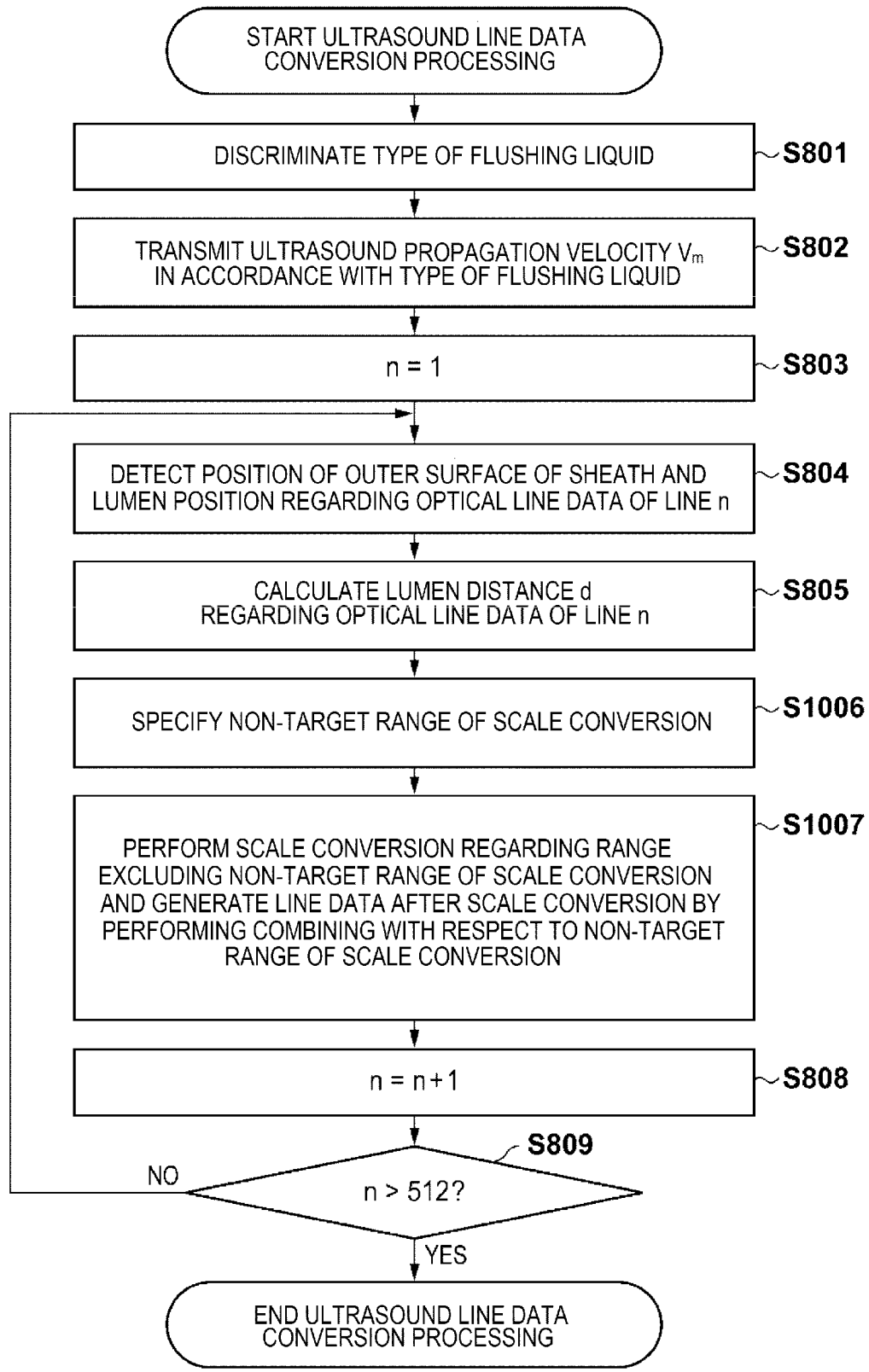
FIG. 10 is a flow chart illustrating another flow of the ultrasound line data conversion processing.

Subsequently, a flow of ultrasound line data conversion processing performed by the signal processing unit 428 will be described. FIG. 10 is a flow chart illustrating a flow of ultrasound line data conversion processing for one frame, performed by the signal processing unit 428.

In each of the steps illustrated in FIG. 10, the same reference numeral and sign are applied to the step similar to each of the steps in FIG. 8 in the first embodiment and the description thereof will be omitted herein. The points different from those in FIG. 8 are as follows.

In Step S1006, the non-target range of scale conversion is specified based on the lumen distance d acquired in Step S805. Specifically, the distance Df (=d) is specified as the non-target range of scale conversion based on the position of the outer surface of the sheath detected in Step S804.

In Step S1007, scale conversion is performed regarding the ultrasound line data within the range excluding the non-target range of scale conversion specified in Step S1006, and the ultrasound line data after scale conversion is generated by being combined with the ultrasound line data within the non-target range of scale conversion.

As is clear from the above description, in the imaging apparatus 100 for diagnosis according to the present embodiment, it is constituted to arrange the ultrasound line data conversion unit so as to perform scale conversion processing for each item of the ultrasound line data.

It is constituted to use the ultrasound propagation velocity in a blood vessel tissue when performing scale conversion processing.

It is constituted to specify the target range of scale conversion after the non-target range of scale conversion is specified by using the lumen distance calculated based on the optical line data.

It is constituted to perform scale conversion processing regarding the specified target range of scale conversion based on the ratio between the ultrasound propagation velocity in accordance with the type of the flushing liquid and the ultrasound propagation velocity in a blood vessel tissue which are used when generating the ultrasound line data before scale conversion.

Accordingly, an error of the scale of an ultrasound tomographic image regardless of the type of the flushing liquid can be reduced.

The detailed description above describes an imaging apparatus for diagnosis, and a program. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis constructing a first tomographic image inside a lumen of a measurement subject body by using an ultrasound signal and an optical signal, the apparatus comprising:
    a transmitting and receiving unit comprising a first transmitting and receiving unit and a second transmitting and receiving unit, wherein the first transmitting and receiving unit performing transmission and reception of the ultrasound signal when rotating in the lumen of the measurement subject body, and wherein the second transmitting and receiving unit performing transmission and reception of the optical signal when rotating in the lumen of the measurement subject body; and
    a processor configured to:
        store an ultrasound propagation velocity in a flushing liquid flowing inside the lumen and an ultrasound propagation velocity in a blood vessel tissue;
        generate ultrasound line data indicating strength of a reflection signal from each position in a transmitting and receiving direction of the ultrasound signal based on the ultrasound propagation velocity in the blood vessel tissue;
        specify a range in which the flushing liquid flows based on the optical signal;
        convert positional information of each position within the range in which the flushing liquid flows regarding the ultrasound line data generated by the processor based on a ratio between the ultrasound propagation velocity in the blood vessel tissue and the ultrasound propagation velocity in the flushing liquid; and
        construct the first tomographic image by using the ultrasound line data which is converted by the processor.

2. The imaging apparatus for diagnosis according to claim 1,
    wherein the lumen is a blood vessel of the measurement subject body; and
    specifying the range in which the flushing liquid flows comprises:
        detecting a position of the lumen of the blood vessel by using optical line data corresponding to the ultrasound line data generated by the processor among items of the optical line data generated based the optical signal;
        detecting a position of an outer surface of a sheath in which the transmitting and receiving unit is disposed, by using the optical line data corresponding to the ultrasound line data generated by the processor; and
        calculating a lumen distance between the position of the lumen of the blood vessel and the position of the outer surface of the sheath.

3. The imaging apparatus for diagnosis according to claim 2,
    wherein the processor converts the positional information by integrating the ratio between the ultrasound propagation velocity in the blood vessel tissue and the ultrasound propagation velocity in the flushing liquid with respect to a distance from the position of the outer surface of the sheath for each position within the range in which the flushing liquid flows.

4. The imaging apparatus for diagnosis according to claim 2,
    wherein the processor is further configured to store the ultrasound propagation velocity by classifying the propagation velocity in accordance with the type of the flushing liquid.

5. The imaging apparatus for diagnosis according to claim 1,
    wherein the ultrasound line data converted by the processor is constructed by combining the ultrasound line data of which the positional information is converted, within the range in which the flushing liquid flows and the ultrasound line data of which the positional information is not converted, out of the range in which the flushing liquid.

6. A method of controlling an image processing apparatus, which processes an image of a target object constructing a first tomographic image inside a lumen of a measurement subject body by using an ultrasound signal and an optical signal, the image processing apparatus comprising a transmitting and receiving unit comprising a first transmitting and receiving unit and a second transmitting and receiving unit, wherein the first transmitting and receiving unit performing transmission and reception of the ultrasound signal when rotating in the lumen of the measurement subject body, and wherein the second transmitting and receiving unit performing transmission and reception of the optical signal when rotating in the lumen of the measurement subject body, the method comprising:
    storing an ultrasound propagation velocity in a flushing liquid flowing inside the lumen and an ultrasound propagation velocity in a blood vessel tissue;
    generating ultrasound line data indicating strength of a reflection signal from each position in a transmitting and receiving direction of the ultrasound signal based on the ultrasound propagation velocity in the blood vessel tissue;
    specifying a range in which the flushing liquid flows based on the optical signal;
    converting positional information of each position within the range in which the flushing liquid flows regarding the ultrasound line data generated based on a ratio between the ultrasound propagation velocity in the blood vessel tissue and the ultrasound propagation velocity in the flushing liquid; and
    constructing the first tomographic image by using the ultrasound line data from the converting of the positional information.

7. The method of controlling an image processing apparatus according to claim 6,
    wherein the lumen is a blood vessel of the measurement subject body; and
    specifying the range in which the flushing liquid flows comprises:
        detecting a position of the lumen of the blood vessel by using optical line data corresponding to the ultrasound line data among items of the optical line data generated based the optical signal;

detecting a position of an outer surface of a sheath in which the transmitting and receiving unit is disposed, by using the optical line data corresponding to the ultrasound line data; and calculating a lumen distance between the position of the lumen of the blood vessel and the position of the outer surface of the sheath.

8. The method of controlling an image processing apparatus according to claim 7, further comprising:

converting the positional information by integrating the ratio between the ultrasound propagation velocity in the blood vessel tissue and the ultrasound propagation velocity in the flushing liquid with respect to a distance from the position of the outer surface of the sheath for each position within the range in which the flushing liquid flows.

9. The method of controlling an image processing apparatus according to claim 7, comprising:

storing the ultrasound propagation velocity by classifying the propagation velocity in accordance with the type of the flushing liquid.

10. The method of controlling an image processing apparatus according to claim 6, further comprising:

constructing the ultrasound line data by combining the ultrasound line data of which the positional information is converted, within the range in which the flushing liquid flows and the ultrasound line data of which the positional information is not converted, out of the range in which the flushing liquid flows.

\* \* \* \* \*